(12) United States Patent
Cho et al.

(10) Patent No.: US 7,138,129 B2
(45) Date of Patent: Nov. 21, 2006

(54) SKIN CARE COMPOSITIONS

(75) Inventors: Suk H. Cho, Idaho Falls, ID (US); Becky Zehntner, Blackfoot, ID (US); Angela M. Tuck, Idaho Falls, ID (US)

(73) Assignee: Melaleuca, Inc., Idaho Falls, ID (US)

( * ) Notice: Subject to any disclaimer, the term of this patent is extended or adjusted under 35 U.S.C. 154(b) by 0 days.

(21) Appl. No.: 10/210,393

(22) Filed: Jul. 31, 2002

(65) Prior Publication Data

US 2004/0022818 A1 Feb. 5, 2004

(51) Int. Cl.
  *A61K 8/02* (2006.01)
  *A61K 8/00* (2006.01)
  *A61K 47/00* (2006.01)
  *A01N 65/00* (2006.01)
  *C11D 17/00* (2006.01)
  *A61K 9/14* (2006.01)

(52) U.S. Cl. ............... 424/401; 424/400; 424/725; 424/732; 424/735; 424/736; 424/765; 424/777; 510/130; 510/135; 510/139; 510/158; 510/159; 514/783

(58) Field of Classification Search ............ 424/400, 424/401, 725, 732, 735, 736, 765, 777; 514/783, 514/844; 510/130, 135, 139, 158, 159
See application file for complete search history.

(56) References Cited

U.S. PATENT DOCUMENTS

| | | | |
|---|---|---|---|
| 2,798,053 A | | 7/1957 | Brown |
| 4,297,374 A | * | 10/1981 | Wess .................... 514/777 |
| 4,590,065 A | * | 5/1986 | Piechota et al. .......... 424/49 |
| 4,871,536 A | * | 10/1989 | Arraudeau et al. ........ 424/59 |
| 4,933,177 A | * | 6/1990 | Grollier et al. ........... 424/74 |
| 5,370,867 A | * | 12/1994 | Okawa et al. .......... 424/78.02 |
| 5,698,199 A | * | 12/1997 | Mori et al. .............. 424/734 |
| 6,200,570 B1 | | 3/2001 | Diwan et al. |
| 6,248,340 B1 | | 6/2001 | Maor et al. |
| 6,348,200 B1 | | 2/2002 | Nakajima et al. |
| 6,383,495 B1 | | 5/2002 | Ramakrishna et al. |
| 6,471,948 B1 | * | 10/2002 | Adamy et al. ............ 424/54 |
| 6,471,983 B1 | * | 10/2002 | Veeger et al. ........... 424/443 |
| 6,555,143 B1 | * | 4/2003 | Miller et al. ............ 424/757 |
| 2003/0049225 A1 | * | 3/2003 | Rucker .................... 424/74 |
| 2003/0108627 A1 | * | 6/2003 | Selzer et al. ............ 424/732 |

FOREIGN PATENT DOCUMENTS

EP 619112 A1 * 10/1994

OTHER PUBLICATIONS

*McCutcheon's—vol. 1: Emulsifiers & Detergents*, 1999, North American Edition, McCutcheon's Division, The Manufacturing Confectioner Publishing Co., Glen Rock, New Jersey (Table of Contents only).

\* cited by examiner

*Primary Examiner*—Sreeni Padmanabhan
*Assistant Examiner*—Marina Lamm
(74) *Attorney, Agent, or Firm*—Fish & Richardson P.C.

(57) ABSTRACT

The invention provides materials and methods for making skin care compositions that contain dried or fresh fruit particles, and also can contain suspending agents, surfactants, emollients, emulsifiers, and/or cationic polymers. The basic fruit components typically are from the pulp and peel of the fruit, which can be specially processed to retain the colors, phytochemicals and nutritive ingredients. The compositions provided herein can contain particles made from whole fruits (minus seeds, leaves, and stems) that have been subjected to drying techniques (e.g., air-drum drying or freeze drying) and then processed into small particles.

8 Claims, No Drawings

SKIN CARE COMPOSITIONS

TECHNICAL FIELD

This invention relates to skin care compositions. In particular, the invention relates to skin care compositions containing suspended particles of fruit.

BACKGROUND

A fruit is a ripened ovary of a female flower. The major types of fruits are aggregate fruits, berries, drupe fruits, false berries, hesperidium fruits, and multiple fruits. Aggregate fruits consist of many tiny seed bearing fruits combined in a single mass (e.g., blackberries). Berry fruits are derived from a single ovary, and contain one or more seeds (e.g., bananas). Drupe fruits are single seed fruits that develop entirely from a single ovary (e.g., plums). False berry fruits consist of many seeded fruits that result from fusion of an ovary and receptacle (e.g., cranberries). Hesperidium fruits include citrus fruits, which develop from a compound ovary into a many seeded, multi-sectional fruit in a tough skin. Multiple fruits are derived from the ovaries and receptacles of multiple flowers on a common base (e.g., pineapple).

Fruits typically contain saccharides (monosaccharides, oligosaccharides and polysaccharides), fiber, various macro and micronutrients, vitamins, and vitamin factors. Many fruits also contain phytochemicals such as phenolic compounds (e.g., flavonoids), which are known to prevent and treat certain disease conditions. Flavonoids also can act as antioxidants that have free radical scavenger properties.

Extracts of fruits and herbs have been used in cosmetic products to provide a perception of naturalness and to take advantage of the benefits of the phytonutrients and phytochemicals contained therein. Such products often contain only insignificant amounts of the extracts, due to the high cost of extracts and in order to minimize discoloration of the finished products. Typically, fruit and herbal extracts are diluted with carriers such as water, alcohol, propylene glycol or butylene glycol. Commercial fruit or botanical extracts generally contain minimal amounts of phytochemicals and other nutrients due to their dilution, long extraction processes, and extended storage time before customers utilize the product.

The use of intact fruit pieces or dried fruit pieces in skin care compositions has not been commercially feasible. Fruit pieces can be hard to process, can potentially cause microorganism contamination, can be difficult to handle during production, often are not aesthetically attractive, can cause suspension problems, and can leave residue on the skin.

SUMMARY

The invention provides materials and methods for making skin care compositions that contain dried or fresh fruit particles, and also can contain suspending agents, surfactants, emollients, emulsifiers, and/or cationic polymers. The basic fruit components typically are from the pulp and peel of the fruit, which can be specially processed to retain the colors, phytochemicals and nutritive ingredients. The compositions provided herein can contain particles made from whole fruits (minus seeds, leaves, and stems) that have been subjected to drying techniques (e.g., air-drum drying or freeze drying) and then processed into small particles.

The invention is based on the discovery that certain processed, dried fruit particles with specific sizes can be incorporated into various skin care compositions and used as effective ingredients in the compositions without using extracts that possess little value other than label claims. The invention is further based on the discovery that fruit particles can be dispersed in skin care compositions using suspending agents to provide a more "natural" look to the compositions. Such skin care compositions can provide superior moisture retention, and can be formulated so as not to leave any fruit residue on the skin when the composition is a leave-on product. The fruit-containing compositions disclosed herein also can provide superior lathering and cleansing qualities, and can be non-irritating to the skin.

The invention provides a skin care composition containing fruit particles. The skin care composition can be a lotion, a cream, a moisturizer, a bath or shower gel, a cleanser, an exfoliating scrub, a bubble bath, or an after bath or shower splash. The fruit particles can be in suspension and can contain dried fruit. The fruit can be selected from the group consisting of: peach, lemon, strawberry, pear, sweet cherry, apricot, blackberry, papaya, mango, orange, raspberry, cranberry, blueberry, kiwi, banana, grapefruit, and vanilla bean. The fruit particles can be in the form of a powder, flakes, or specks, and can be between about 10 microns and about 2500 microns in diameter (e.g., between about 100 microns and about 200 microns in diameter). The fruit particles can have a tap density between about 0.1 g/mL and about 0.6 g/mL (e.g., between about 0.2 g/mL and about 0.45 g/mL). The fruit particles can be, by weight, about 0.01% to about 40% of the composition (e.g., about 0.1% to about 15% of the composition).

The skin care composition can further contain a suspending agent. The suspending agent can be, by weight, about 0.001% to about 10% of the composition (e.g., about 0.01% to about 5% of the composition). The suspending agent can be xanthan gum or modified starch.

The skin care composition can further contain a cationic polymer, an emollient, or one or more surfactants. The cationic polymer can be, by weight, about 0.001% to about 10% of the composition (e.g., about 0.05% to about 6% of the composition). The cationic polymer can be cellulose or a quaternized protein. The surfactant can be, by weight, about 0.01% to about 40% of the composition (e.g., about 0.2% to about 15% or about 0.5% to about 10% of the composition). The surfactant can be an anionic surfactant (e.g., sodium oleyl sulfate, ammonium lauryl sulfonate, ammonium lauryl sulfate, sodium lauryl sulfate, sodium cocoyl sulfate, sodium octylsulfosuccinate, ammonium lauryl sulfosuccinate, sodium lauryl sarcosinate, sodium alphaolefin sulfonate, sodium cocosulfate sulfate, ammonium or sodium salts of lauryl sulfate, ammonium or sodium palimitate, disodium polyglucoside sulfosuccinate, disodium oleamido MIPA sulfosuccinate, sodium cocoyl glutamate, sodium lauroyl sarcosinate, sodium cocoyl isethionate, sodium laureth sulfate, or lauric acid).

The skin care composition can further contain a suspending agent, a surfactant, and an emollient. The skin care composition can further contain a suspending agent, a surfactant, and a cationic polymer. The skin care composition can further contain a suspending agent, an emulsifier, and an emollient.

In another aspect, the invention features a method for making a skin care composition containing fruit particles. The method can involve combining fruit particles with a suspending agent and a component selected from the group consisting of a surfactant, an emollient, an emulsifier, and a cationic polymer.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and from the claims.

DETAILED DESCRIPTION

The invention provides materials and methods for making skin care compositions that contain dried or fresh fruit particles, and also can contain suspending agents, surfactants, emollients, emulsifiers, and/or cationic polymers. The basic fruit components typically are from the pulp and peel of the fruit, which can be specially processed to retain the colors, phytochemicals and nutritive ingredients. The compositions provided herein can contain particles made from whole fruits (minus seeds, leaves, and stems) that have been subjected to drying techniques (e.g., air-drum drying or freeze drying) and then processed into small particles.

The components described herein can be combined in any formulation, including those provided in the Examples below. Compositions of the invention typically are skin care products, including, without limitation, lotions, creams, soaps, cleansers, moisturizers, bubble baths, bath or shower gels, exfoliating scrubs, and after-bath or shower splashes. The skin care compositions provided by the invention can contain any of the components disclosed herein, in any amounts and any combination. For example, a composition can be a cleansing product that contains fruit particles, a surfactant, a suspending agent, and an emollient and/or a cationic polymer. In another embodiment, a composition can be a lotion or cream that contains fruit particles, an emulsifier, a suspending agent, and one or more emollients.

Fruits: The compositions provided herein contain fruit particles. As used herein, the term "fruit particles" refers to pieces of fresh or dried fruit from which the seed(s), stem, and leaves have been removed. A "fruit particle" is between about 10 microns and about 2500 microns in diameter or width (e.g., between about 25 microns and about 2000 microns, between about 50 microns and about 1000 microns, between about 75 microns and about 500 microns, or between about 100 microns and about 200 microns in diameter or width). Furthermore, a "fruit particle" can have a tap density between about 0.1 g/mL and about 0.6 g/mL (e.g., between about 0.2 g/mL and about 0.45 g/mL).

The fruit can be fresh-cut fruit or dried fruit, and can be in the form of a powder, flakes, or specks. Typically, the compositions provided herein contain dried fruit in the form of flakes or powder. Whole fruits (minus seeds, leaves, and stems) can be subjected to any suitable drying technique (e.g., sun-drying, vacuum-drying, kiln-drying, air-drum drying, or freeze-drying).

The fruit particles can be from all parts of the fruit other than the stem, leaves, and seeds, and thus can include the core and the peel, which contain colorants, phytochemicals (e.g., flavonoids), macrominerals, microminerals, and vitamins. The basic fruit components included in the compositions provided herein can be specially processed in order to retain their colors, phytochemicals, and nutritive ingredients. The dried fruits used herein also contain saccharides, which can have complex and diverse structures and can add moisture retention qualities to the compositions provided herein.

Compositions of the invention can contain fruit particles such as, without limitation, peach powder, lemon powder, strawberry powder, pear powder, sweet cherry powder, apricot powder, blackberry powder, papaya powder, mango powder, orange powder, apple fiber, peach flakes, golden apple flakes, pear pieces, raspberry flakes, pear flakes (e.g., Williams Pear flakes), orange flakes, papaya flakes, citrus pectin cellulose II (e.g., orange pulp and peel), cranberry flakes, mango flakes, blueberry flakes, kiwi flakes, banana flakes, strawberry flakes, grapefruit powder, cranberry fiber, lemon flakes, apricot flakes, sweet cherry flakes, vanilla bean specks (e.g., Madagascar Bourbon vanilla bean specks), and apple flakes. Vegetable particles (e.g., cucumber peel) also can be included in compositions of the invention. These flakes, fibers, and powders can be obtained from International Botanical and Specialty Products, Inc. of Wisconsin, and Freeman Industries, L.L.C. (Tuckahoe, N.Y.), for example.

The compositions provided herein can have a fruit content that is between about 0.01% and about 40% by weight (e.g., between about 0.05% and about 25% by weight). Typically, the compositions have a fruit content between 0.1% and 15% by weight. The fruit pieces (dried or freshly cut) can be visible and dispersed within the compositions.

Suspending agents: Compositions of the invention can incorporate one or more suspending agents to serve as a thickener in order to disperse and suspend the fruit particles. A suspending agent can prevent the fruit from settling to the bottom of the compositions or rising to the top of the compositions. A suspending agent can be, for example, a crosslinked polycarboxylate polymer (e.g., a carboxyvinyl polymer). Such compounds are disclosed in U.S. Pat. No. 2,798,053, for example, and are commercially available from B. F. Goodrich Company, New York, N.Y. under the trade name Carbopol®. Other suitable crosslinked polycarboxylate polymers include products marketed under the trade name Polygel, which is available from 3V.

A suspending agent also can be xanthan gum or a cellulose analog. Xanthan gum is a biopolysaccharide obtained from the growth of *Xanthomonas* spp. Suitable xanthan gums include, for example, products sold under the trade names Keltrol® and Kelzan® by CP Kelco, Inc. (Chicago, Ill.), and products sold under the trade names Rhodopol® and Rhodigel™ by Rhodia, Inc (Cranbury, N.J.). Suitable cellulose analogs include hydroxypropylmethylcellulose and hydroxyethylcellulose. Cellulose analogs also include modified starch and starch-based modifiers, which can be produced by hydroxypropylation of a waxy maize starch. Cellulose analogs also can be sulfated or phosphorylated. Modified starches include products sold under the name Structure® XL by National Starch & Chemical (Bridgewater, N.J.). In addition, a suspending agent can be clay.

When the suspending agent is a crosslinked polycarboxylate polymer such as Carbopol® 940, hydration of the thickener can be avoided by dissolving a weak acid in water prior to dispersing the thickener in the water. For example, citric acid can be dissolved in water prior to addition of the thickener, and a pH adjusting agent can be added followed by all of the remaining ingredients (e.g., surfactants, conditioning agents, vitamins, preservatives, fragrance, and/or colorant).

For compositions in which the ratio of suspending agent to water is high, the thickener/suspending agent can be preblended with a non-aqueous ingredient prior to the addition of water. For example, a suspending agent can be dry blended with a solid ingredient or dispersed in a non-aqueous liquid ingredient prior to addition of water.

The compositions provided herein can contain, by weight, about 0.001% to about 5% suspending agents/thickeners. Typically, the compositions contain about 0.01% to about 2% suspending agents by weight.

Cationic Polymers: The compositions provided herein can contain cationic polymers to increase retention of the fruit particles and thus enhance the moisturization capabilities of the compositions. Suitable cationic polymers include cationic cellulose, cationic proteins, and cationic polymers that contain vinyl group backbones consisting of amino and/or quaternary ammonium monomers. Cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salts, diallyl quaternary ammonium salts, and vinyl quaternary ammonium monomers with cationic, nitrogen-containing rings (e.g., pyridinium, imidazolium, and quaternized pyrrolidine). Such monomers can be copolymerized with noncationic monomers. Specific examples of monomers include, without limitation, vinylpyrrolidone, hydroxyethylmethacrylate, methyl methacrylate, acrylic acid, hydroxyethylacrylic acid, butyl methacrylate, vinylacetate, crotonic acid, and acrylamide.

Monomers such as those described above can form homopolymers and/or copolymers (e.g., film forming polymers) having glass transition temperatures (Tg) ranging from about −20° C. to 150° C. (e.g., about −10° C. to about 100° C., or about 0° C. to about 80° C.). Film forming polymers can be soluble and/or dispersible in water and/or alcohol. Such polymers typically have molecular weights of at least about 100 to about 2,500,000 Daltons (e.g., about 500 to about 2,000,000 Daltons, or about 1,000 to about 1,000,000 Daltons).

Examples of suitable cationic polymers also include, without limitation, hydroxypropyltrimonium honey, cocodimonium silk amino acids, cocodimonium hydroxypropyl hydrolyzed wheat or silk protein, polyquaternium-5, polyquaternium-11, polyquaternium-2, polyquaternium-4, polyquaternium-6, polyquaternium-7, polyquaternium-14, polyquaternium-16, polyquaternium-22, polyquaternium-10, and guar hydroxypropyltrimonium chloride. Other suitable cationic polymers include quaternized proteins (e.g., quaternized natural proteins) and cellulose.

Cationic polymers can be obtained from, for example, Croda, Inc. (Parsippany, N.J.), Arch Personal Care Products, L.P. (South Plainfield, N.J.), National Starch & Chemical, and Rhodia, Inc.

Cationic polymers can be included in compositions of the invention in at least an amount effective to increase the substantivity of the fruit. Compositions typically contain about 0.001% to about 10% cationic polymers by weight (e.g., about 0.01% to about 8%, or about 0.05% to about 6% cationic polymers by weight).

Surfactants: The compositions provided herein also can contain one or more surfactants that can be used to achieve a "clean lather" feel when included in skin cleanser compositions. Surfactants can be, for example, anionic surfactants, nonionic surfactants, amphoteric surfactants, and zwitterionic surfactants.

Suitable anionic surfactants include, for example, alkylsulfate, alkylolefin sulfonate, alkyl ether sulfate, alkylarylsulfonates, alkylsuccinate, alkyl sulphosuccinates, acyl taurates, acyl glutamates, N-alkyl sarcosinates, alkylphosphate, alkyl ether phosphates, alkyl ether carboxylates, and sodium, potassium, magnesium, alkonol ammonium, quaternized or protonated alkanolamine, and alkylammonium salts of such compounds. The alkyl and acyl groups can contain about eight to about 20 carbon atoms, and can be unsaturated. The alkyl ether sulfates, alkyl ether phosphates, and alkyl ether carboxylates can contain one to about 10 ethylene oxide or propylene oxide groups (or a mixture thereof) per molecule, and typically contain about two to about five ethylene oxide units per molecule. Examples of suitable anionic surfactants include, without limitation, sodium oleyl sulfate, ammonium lauryl sulfonate, ammonium lauryl sulfate, sodium lauryl sulfate, sodium cocoyl sulfate, sodium octylsulfosuccinate, ammonium lauryl sulfosuccinate, sodium lauryl sarcosinate, sodium alpha-olefin sulfonate, sodium cocosulfate sulfate, ammonium or sodium salts of lauryl sulfate, ammonium or sodium palimtate, disodium polyglucoside sulfosuccinate, disodium oleamido MIPA sulfosuccinate, sodium cocoyl glutamate, sodium lauroyl sarcosinate, sodium cocoyl isethionate, sodium laureth sulfate, lauric acid, and mixtures thereof.

The anionic surfactants included in compositions of the present invention typically are present in at least an amount effective to provide lathering and cleansing properties while being non-irritating. The compositions provided herein can contain about 0.01% to about 40% anionic surfactants by weight (e.g., about 0.2% to about 15%, or about 0.5% to about 10% anionic surfactants by weight).

Amphoteric and zwitterionic surfactants also can be used in the compositions provided herein. Suitable amphoteric and zwitterionic surfactants include, for example, alkyl amine oxides, alkyl betaines, alkylamidopropylbetaines, alkylsulfobetaines, alkylglycinates, alkycarboxyglycinates, alkylamphopropionates, alkylamphoglyciantes, alkylamidohydroxysultaines, alkyl amphoacetates, and alkyl amphodiacetates. Specific examples of such compounds include, without limitation, laurylamine oxide, cocamidopropyl betaine, cocoamphopriopionate, and cocodimethyl sulphopropylbetaine. Cocamidopropyl betaine, disodium cocoamphodiacetate, cocamidopropyl hydroxysultaine, alkyl amine oxide, and mixtures thereof can be particularly useful in compositions of the present invention.

Amphoteric and zwitterionic surfactants typically are present in at least an amount effective to provide lathering and cleansing, while being non-irritating. Compositions of the invention can contain, for example, about 0.01% to about 40% amphoteric and/or zwitterionic surfactants by weight (e.g., about 0.2% to about 15%, or about 0.5% to about 10% amphoteric and/or zwitterionic surfactants by weight).

The compositions provided herein also can contain nonionic surfactants. Suitable nonionic surfactants include alkyl ethoxylates, which can be prepared as the condensation product of: (a) one mole of a saturated or unsaturated straight or branched chain fatty alcohol or fatty acid having a chain length of about ten to about 20 carbon atoms, and (b) about 4 to about 40 moles of ethylene oxide or propyleneoxide, alkyl polyglycosides, and alkylalkanolamides. Examples of such compounds include, without limitation, laurylamido diethanolamine (DEA), palmitamide monoethanolamide (MEA), cocoamide MEA, coco mono-isopropanolamide, glycol stearate, stearyamidopropyl dimethylamine, glycol distearate, polyoxyethylene sorbitan monolaurate and monostearates, cetyl alcohol, stearyl alcohol, cetereth-20, and alkylpolyglucoside.

The compositions provided herein can contain anionic surfactants and zwitterionic (or amphoteric) surfactants in a ratio of about 5:1 to about 1:5. Nonionic surfactants also can be added to this combination of surfactants to improve lathering, for example.

Surfactants other than those listed herein also can be included in compositions of the invention. Such surfactants can be found in *McCutcheon's Emulsifiers and Detergents: 1999 North American Edition* (McCutcheon Div., MC Publishing Co.), for example. Suitable surfactants can be obtained from, for example, Stepan Company (Northfield, Ill.), Pilot Chemical Company (Santa Fe Springs, Calif.), McIntyre Group, LTD (University Park, Ill.), Clariant Corporation (Charlotte, N.C.), and Cognis Care Chemicals (Cincinnati, Ohio).

Emulsifiers: The compositions provided herein also can contain emulsifiers. Examples of suitable emulsifiers include, without limitation, stearic acid, cetyl alcohol, PEG-100, stearate and glyceryl stearate, cetearyl glucoside, polysorbate 20, ceteareth-20, cetyl alcohol, cetearyl alcohol, self-emulsifying wax (e.g., Lipowax P), cetyl palmitate, stearyl alcohol, lecithin, hydrogenated lecithin, steareth-2, steareth-20, and polyglyceryl-2 stearate. Other emulsifiers also can be included in the compositions of the present invention without departing from the principles taught herein. Examples of such emulsifiers include those found in *McCutcheon's Emulsifiers and Detergents: 1999 North American Edition* (supra). Emulsifiers can be obtained from, for example, Lipo Chemicals, Inc. (Paterson, N.J.), Croda, Inc., Goldschmidt AG (Essen, Germany), and Uniqema, Inc. (New Castle, Del.).

Silicone derivatives: The compositions provided herein can include silicone to impart lubrication qualities. Suitable silicones include those that are emulsified, for example. Silicones that can be used in the skin care compositions provided herein include, without limitation, nonvolatile silicone fluids such as dimethicone copolyol, cyclomethicone, polydimethylsiloxane, cyclic dimethyl polysiloxane, aminosilicones and phenylsilicones. Cyclopentasiloxane, dimethicone copolyol (a polymer of dimethylsiloxane with polyoxyethylene and/or polyoxypropylene), cetyl dimethicone, cetyl dimethiconecopolyol, and aminopropyl PEG-7 PEG-3 dimethicone copolyol also can be particularly useful. Such silicones are readily available from Goldschmidt A G, General Electric (Waterford, N.Y.), and Dow Corning Corporation (Midland, Mich.).

Silicones used in compositions of the present invention typically have a viscosity ranging from about 50 cst to about 2,000 cst (e.g., about 100 cst to about 1,500,000 cst, or about 150 cst to about 1,000,000 cst) at 25° C. Silicone can be present in at least an amount effective to provide lubrication properties to the composition. The compositions provided herein can contain, by weight, from 0.001% to about 5.0% silicone (e.g., about 0.01% to about 4%, or about 0.05% to about 2.5% silicone by weight).

Vitamins: The composition provided herein can contain one or more vitamins, such as provitamin B (e.g., panthenol, phytantriol, or ethylpanthenol), vitamin A acetate, vitamin A palmitate, retinol, retinoic acid, vitamin D, vitamin E, vitamin A, tocopheryl acetate, tocopheryl palmitate, vitamin C (ascorbic acid), ascorbyl glucoside, magnesium ascorbyl phosphate, ascorbyl palmitate, and mixtures thereof. Such vitamins can be obtained from Roche Vitamins, Inc. (Parsippany, N.J.), and BASF Corporation (Mount Olive, N.J.), for example.

Botanical extracts: Compositions of the invention also can contain herbal and/or fruit extracts. Suitable herbal extracts can be, for example, standardized extracts that are dispersible and/or soluble in aqueous medium. Examples of herbal extracts include, without limitation, chamomile, rosemary, aloe, nettle, *Centella asiatica,* ginkgo biloba, betula, and witch hazel. Such extracts typically are delivered in a carrier such as water, propylene glycol, hydroalcohol, glycerine, or butylene glycol. Powdered extracts with nutritional quality can be used, including, without limitation, powders of green tea, grape skin, grapefruit, bilberry, blueberry, Ginkgo biloba, soy isoflavones, black cohosh, St. John's wort, echinacea, chamomile, rosemary, aloe, nettle, and *Centella asiatica.* Botanical extracts can be obtained from, for example, Active Organics (Lewisville, Tex.), New Age Botanicals (Garland, Tex.), Triarco Industries (Wayne, N.J.), and Aloecorp (Broomfield, Colo.).

Essential oils: The compositions provided herein also can contain one or more essential oils. Suitable oils include, without limitation, unsaturated oils such as canola oil, evening primrose oil, jojoba oil, flax seed oil, sunflower oil, soya oil, apricot kernel oil, safflower oil, kukui nut oil, fish oil, and mixtures thereof. Essential oils can be obtained from Desert Whale Jojoba Co., Inc. (Tucson, Ariz.), FloraTech Americas (Gilbert, Ariz.), Biochemicals International Ltd. (Satellite Beach, Fla.), Arista Industries, Inc. (Wilton, Conn.), and International Botanical and Specialty Products, Inc.

Other optional ingredients: The compositions provided herein can contain a variety of optional ingredients, including, without limitation, hydrotropes, preservatives, fragrances, colorants, pH adjusting agents, and the like, without departing from the principles taught herein.

pH adjustment: The final pH of the undiluted product typically is between 4.0 and 8.5 (e.g., 5.5 to 8.0). To obtain such a pH, the pH of the composition can be adjusted using a pH-adjusting agent, for example. It will be appreciated that pH adjustment can be accomplished with any of a wide variety of acids should the composition have a pH that is too high (e.g., greater than 8.5 before adjustment). Likewise, pH adjustment can be accomplished with any of a wide variety of bases should the composition have a pH that is too low (e.g., less than 4.0 before adjustment). The compositions provided herein typically have greater stability when the pH is between pH 4.0 to 8.5. In addition, compositions having a pH within this range tend to be aesthetically pleasing and compatible with the skin.

The invention will be further described in the following examples, which do not limit the scope of the invention described in the claims.

EXAMPLES

Example 1

Body Cleanser

A body cleanser composition was prepared by combining the following ingredients. The amount of each ingredient is provided as percent by weight.

| Ingredient | W/W % Used |
| --- | --- |
| Water | Q.S. to 100 |
| Hydroxypropyl Starch Phosphate Ester | 0.200 |
| Citric Acid | 0.300 |

-continued

| Ingredient | W/W % Used |
| --- | --- |
| Green Tea Extract (Powder) | 0.500 |
| Aloe Barbadensis (Powder) | 0.500 |
| Grape Seed Extract (Powder) | 0.100 |
| Polyquaternium 10 | 0.300 |
| Glycol Distearate | 0.900 |
| PEG-120 Glutamate | 5.000 |
| Glycerin | 5.000 |
| Sunflower Seed Oil | 0.060 |
| Canola Oil | 0.120 |
| Evening Primrose Oil | 0.060 |
| Apricot Oil | 0.060 |
| Hydroxypropyltrimonium Honey | 0.500 |
| Disodium Oleamido MIPA Sulfosuccinate | 2.500 |
| Cocamidopropyl Betaine | 10.500 |
| Sodium Cocosulfate | 13.000 |
| Cetyl Alcohol | 0.500 |
| Lauric Acid | 1.000 |
| PEG-7 Glyceryl Cocoate | 2.000 |
| Polyglyceryl-3 Caprylate | 0.500 |
| Preservative | 0.750 |
| Vitamin A & D3 | 0.050 |
| Ascorbyl Palmitate | 0.001 |
| Dimethicone Copolyol | 0.500 |
| Melaleuca Oil | 0.020 |
| Potassium Sorbate | 0.200 |
| Apple Fibers | 1.000 |
| Apple Fruit Flakes | 1.000 |
| Cranberry Flakes | 0.200 |
| Fragrance | 4.000 |
| BHT | 0.050 |
| Sodium Copper Chlorophyllin | 0.001 |
| Alfalfa Extract | 0.030 |

Example 2

Body Cleanser

A body cleanser composition was prepared by combining the following ingredients. The amount of each ingredient is provided as percent by weight.

| Ingredient | W/W % Used |
| --- | --- |
| Water | Q.S. to 100 |
| Xanthan gum | 0.200 |
| Citric Acid | 0.300 |
| Green Tea Extract (Powder) | 0.100 |
| Aloe Barbadensis (Powder) | 0.400 |
| Grape Seed Extract (Powder) | 0.050 |
| Polyquaternium 10 | 0.300 |
| Glycol Distearate | 0.900 |
| PEG-120 Glutamate | 2.000 |
| Glycerin | 1.000 |
| Sunflower Seed Oil | 0.060 |
| Canola Oil | 0.120 |
| Evening Primrose Oil | 0.060 |
| Apricot Oil | 0.060 |
| Hydroxypropyltrimonium Honey | 0.500 |
| Disodium Oleamido MIPA Sulfosuccinate | 2.500 |
| Cocamidopropyl Betaine | 10.500 |
| Sodium Cocosulfate | 13.000 |
| Cetyl Alcohol | 0.500 |
| Lauric Acid | 1.000 |
| PEG-7 Glyceryl Cocoate | 2.000 |
| Polyglyceryl-3 Caprylate | 0.500 |
| d-Tocopheryl Acetate | 0.100 |
| Vitamin A & D3 | 0.100 |
| Ascorbyl Palmitate | 0.100 |
| Dimethicone Copolyol | 0.500 |
| Melaleuca Oil | 0.001 |
| Saccharide Isomerate | 0.200 |

-continued

| Ingredient | W/W % Used |
| --- | --- |
| Potassium Sorbate | 0.200 |
| Preservative | 0.050 |
| Apple Fibers | 0.200 |
| Apple Fruit Flakes | 0.800 |
| Cranberry Flakes | 0.200 |
| Fragrance | 4.000 |
| Sodium Copper Chlorophyllin | 0.000 |
| Alfalfa Extract | 0.030 |

Example 3

Body Cleanser

A body cleanser composition was prepared by combining the following ingredients. The amount of each ingredient is provided as percent by weight.

| Ingredient | W/W % Used |
| --- | --- |
| Water | Q.S. to 100 |
| Xanthan Gum | 0.200 |
| Citric Acid | 0.300 |
| Green Tea Extract (Powder) | 0.001 |
| Aloe Barbadensis (Powder) | 0.001 |
| Grape Seed Extract (Powder) | 0.001 |
| Polyquaternium 10 | 0.300 |
| Glycol Distearate | 0.900 |
| PEG-120 Glutamate | 0.001 |
| Glycerin | 4.000 |
| Sunflower Seed Oil | 0.060 |
| Canola Oil | 0.120 |
| Evening Primrose Oil | 0.060 |
| Apricot Oil | 0.060 |
| Hydroxypropyltrimonium Honey | 0.500 |
| Disodium Oleamido MIPA Sulfosuccinate | 2.500 |
| Cocamidopropyl Betaine | 10.500 |
| Sodium Cocosulfate | 13.000 |
| Cetyl Alcohol | 0.500 |
| Lauric Acid | 1.000 |
| PEG-7 Glyceryl Cocoate | 2.000 |
| Polyglyceryl-3 Caprylate | 0.500 |
| d-Tocopheryl Acetate | 0.050 |
| Vitamin A & D3 | 0.001 |
| Ascorbyl Palmitate | 0.001 |
| Dimethicone Copolyol | 0.500 |
| Potassium Sorbate | 0.200 |
| Grapefruit Seed Extract | 0.050 |
| Apple Fibers | 0.200 |
| Apple Fruit Flakes | 0.400 |
| Cranberry Flakes | 0.100 |
| Fragrance | 2.500 |
| BHT | 0.050 |
| Sodium Copper Chlorophyllin | 0.010 |
| Alfalfa Extract | 0.100 |

Example 4

Body Cleanser

A body cleanser composition was prepared by combining the following ingredients. The amount of each ingredient is provided as percent by weight.

| Ingredient | W/W % Used |
| --- | --- |
| Water | Q.S. to 100 |
| Xanthan Gum | 0.200 |
| Citric Acid | 0.300 |

-continued

| Ingredient | W/W % Used |
| --- | --- |
| Green Tea Extract (Powder) | 0.001 |
| Aloe Barbadensis (Powder) | 0.001 |
| Grape Seed Extract (Powder) | 0.001 |
| Polyquaternium 10 | 0.300 |
| Glycol Distearate | 0.900 |
| PEG-120 Glutamate | 0.001 |
| Glycerin | 1.000 |
| Sunflower Seed Oil | 0.060 |
| Canola Oil | 0.120 |
| Evening Primrose Oil | 0.060 |
| Apricot Oil | 0.060 |
| Hydroxypropyltrimonium Honey | 0.500 |
| Disodium Oleamido MIPA Sulfosuccinate | 2.500 |
| Cocamidopropyl Betaine | 10.500 |
| Sodium Cocosulfate | 13.000 |
| Cetyl Alcohol | 1.000 |
| Lauric Acid | 1.000 |
| PEG-7 Glyceryl Cocoate | 2.000 |
| Polyglyceryl-3 Caprylate | 0.500 |
| d-Tocopheryl Acetate | 0.050 |
| Vitamin A & D3 | 0.001 |
| Ascorbyl Palmitate | 0.001 |
| Dimethicone Copolyol | 0.500 |
| Melaleuca Oil | 0.001 |
| Saccharide Isomerate | 0.200 |
| Potassium Sorbate | 0.200 |
| Grapefruit Seed Extract | 0.050 |
| Exhausted Vanilla Bean Specks | 0.200 |
| Peach Fruit Flakes | 0.400 |
| Pure Vanilla Extract | 0.100 |
| Fragrance | 4.000 |

Example 5

Body Cleanser

A body cleanser composition was prepared by combining the following ingredients. The amount of each ingredient is provided as percent by weight.

| Ingredient | W/W % Used |
| --- | --- |
| Water | Q.S. to 100 |
| Xanthan Gum | 0.200 |
| Citric Acid | 0.300 |
| Green Tea Extract (Powder) | 0.001 |
| Aloe Barbadensis (Powder) | 0.001 |
| Grape Seed Extract (Powder) | 0.001 |
| Polyquaternium 10 | 0.300 |
| Glycol Distearate | 0.900 |
| Glycerin | 1.000 |
| Sunflower Seed Oil | 0.060 |
| Canola Oil | 0.120 |
| Evening Primrose Oil | 0.060 |
| Apricot Oil | 0.060 |
| Hydroxypropyltrimonium Honey | 0.500 |
| Disodium Oleamido MIPA Sulfosuccinate | 2.500 |
| Cocamidopropyl Betaine | 10.500 |
| Sodium Cocosulfate | 13.000 |
| Cetyl Alcohol | 0.500 |
| Lauric Acid | 1.000 |
| PEG-7 Glyceryl Cocoate | 2.000 |
| Polyglyceryl-3 Caprylate | 0.500 |
| d-Tocopheryl Acetate | 0.050 |
| Vitamin A & D3 | 0.001 |
| Ascorbyl Palmitate | 0.001 |
| Dimethicone Copolyol | 0.500 |
| Melaleuca Oil | 0.001 |
| Saccharide Isomerate | 0.200 |
| Potassium Sorbate | 0.200 |

-continued

| Ingredient | W/W % Used |
| --- | --- |
| Grapefruit Seed Extract | 0.050 |
| Pear Fruit Chunks | 0.400 |
| Raspberry Fruit Flakes | 0.400 |
| Fragrance | 4.000 |
| Carmine | 0.090 |

Example 6

Body Cleanser

A body cleanser composition was prepared by combining the following ingredients. The amount of each ingredient is provided as percent by weight.

| Ingredient | W/W % Used |
| --- | --- |
| Water | Q.S. to 100 |
| Hydroxypropyl Starch Phosphate Ester | 0.200 |
| Citric Acid | 0.300 |
| Green Tea Extract (Powder) | 0.001 |
| Aloe Barbadensis (Powder) | 0.001 |
| Grape Seed Extract (Powder) | 0.001 |
| Polyquaternium 10 | 0.300 |
| Glycol Distearate | 0.900 |
| Glycerin | 1.000 |
| Sunflower Seed Oil | 0.060 |
| Canola Oil | 0.120 |
| Evening Primrose Oil | 0.060 |
| Apricot Oil | 0.060 |
| Hydroxypropyltrimonium Honey | 0.500 |
| Disodium Oleamido MIPA Sulfosuccinate | 2.500 |
| Cocamidopropyl Betaine | 10.500 |
| Sodium Cocosulfate | 13.000 |
| Cetyl Alcohol | 0.500 |
| Lauric Acid | 1.000 |
| PEG-7 Glyceryl Cocoate | 2.000 |
| Polyglyceryl-3 Caprylate | 0.500 |
| d-Tocopheryl Acetate | 0.500 |
| Vitamin A & D3 | 0.500 |
| Ascorbyl Palmitate | 0.100 |
| Dimethicone Copolyol | 0.500 |
| Melaleuca Oil | 0.500 |
| Saccharide Isomerate | 0.200 |
| Potassium Sorbate | 0.200 |
| Preservative | 0.050 |
| Pear Fruit Chunks | 1.000 |
| Raspberry Fruit Flakes | 1.000 |
| Fragrance | 4.000 |
| Carmine | 0.001 |

Example 7

Body Lotion

A body lotion composition was prepared by combining the following ingredients. The amount of each ingredient is provided as percent by weight.

| Ingredient | W/W % Used |
| --- | --- |
| Water | Q.S. to 100 |
| Citric Acid | 0.100 |
| Aloe Barbadensis (Powder) | 0.001 |
| Grape Seed Extract (Powder) | 0.001 |

-continued

| Ingredient | W/W % Used |
|---|---|
| Green Tea Extract (Powder) | 0.001 |
| Glycerin | 3.000 |
| Lactic Acid, Arginine | 1.000 |
| Glycerol Monostearate SE | 3.000 |
| Cetyl Alcohol | 4.000 |
| Stearic Acid | 4.000 |
| Cetearyl Glucoside | 2.000 |
| Melaleuca Oil | 0.250 |
| Octyl Palmitate | 3.000 |
| Polysorbate 20 | 2.500 |
| Dimethicone Copolyol | 1.500 |
| Evening Primrose Oil | 0.125 |
| Apricot Kernel Oil | 0.125 |
| Sunflower Seed Oil | 0.125 |
| Canola Oil | 0.125 |
| Decyl Oleate | 3.000 |
| Squalane | 4.500 |
| Saccharide Isomerate | 1.400 |
| Preservative | 0.900 |
| Oat Extract | 0.100 |
| Ascorbyl Glucoside | 0.100 |
| Vitamin A & D3 Blend | 0.250 |
| d-Tocopherol Acetate | 0.250 |
| Potassium Sorbate | 0.200 |
| Peach Fruit Flakes | 1.000 |
| Pure Vanilla Extract | 0.500 |
| Fragrance | 2.000 |

Example 8

Body Lotion

A body lotion composition was prepared by combining the following ingredients. The amount of each ingredient is provided as percent by weight.

| Ingredient | W/W % Used |
|---|---|
| Water | QS to 100 |
| Hydroxypropyl Starch Phosphate Ester | 0.200 |
| Citric Acid | 0.100 |
| Aloe Barbadensis (Powder) | 0.001 |
| Grape Seed Extract (Powder) | 0.001 |
| Green Tea Extract (Powder) | 0.001 |
| Glycerin | 3.000 |
| Lactic Acid, Arginine | 1.000 |
| Sodium Hydroxide | 0.750 |
| Glycerol Monostearate SE | 3.000 |
| Cetyl Alcohol | 4.000 |
| Stearic Acid | 4.000 |
| Cetearyl Glucoside | 2.000 |
| Melaleuca Oil | 0.001 |
| Octyl Palmitate | 3.000 |
| Polysorbate 20 | 2.500 |
| Evening Primrose Oil | 0.125 |
| Apricot Kernel Oil | 0.125 |
| Sunflower Seed Oil | 0.125 |
| Canola Oil | 0.125 |
| Decyl Oleate | 3.000 |
| Squalane | 4.500 |
| Saccharide Isomerate | 1.400 |
| Oat Extract | 0.100 |
| Ascorbyl Glucoside | 0.001 |
| Vitamin A & D3 Blend | 0.050 |
| d-Tocopherol Acetate | 0.050 |
| Grapefruit Seed Extract | 0.050 |
| Potassium Sorbate | 0.200 |
| Golden Apple Fruit Flakes | 0.400 |
| Cranberry Fruit Flakes | 0.100 |
| Fragrance | 1.500 |

-continued

| Ingredient | W/W % Used |
|---|---|
| Sodium Copper Chlorophyllin | 0.006 |
| Alfalfa Extract | 0.050 |

Example 9

Body Lotion

A body lotion composition was prepared by combining the following ingredients. The amount of each ingredient is provided as percent by weight.

| Ingredient | W/W % Used |
|---|---|
| Water | Q.S. to 100 |
| Citric Acid | 0.100 |
| Aloe Barbadensis (Powder) | 0.100 |
| Grape Seed Extract (Powder) | 0.200 |
| Green Tea Extract (Powder) | 0.200 |
| Glycerin | 3.000 |
| Lactic Acid, Arginine | 1.000 |
| Sodium Hydroxide | 0.750 |
| Glycerol Monostearate SE | 3.000 |
| Cetyl Alcohol | 4.000 |
| Stearic Acid | 4.000 |
| Cetearyl Glucoside | 2.000 |
| Melaleuca Oil | 0.250 |
| Octyl Palmitate | 3.000 |
| Polysorbate 20 | 2.500 |
| Dimethicone Copolyol | 1.500 |
| Evening Primrose Oil | 0.125 |
| Apricot Kernel Oil | 0.125 |
| Sunflower Seed Oil | 0.125 |
| Canola Oil | 0.125 |
| Decyl Oleate | 3.000 |
| Squalane | 4.500 |
| Saccharide Isomerate | 1.400 |
| Oat Extract | 0.100 |
| Ascorbyl Glucoside | 0.050 |
| Vitamin A & D3 Blend | 0.300 |
| Preservative | 0.900 |
| d-Tocopherol Acetate | 0.500 |
| Potassium Sorbate | 0.200 |
| Williams Pear Fruit Flakes | 0.400 |
| Raspberry Fruit Flakes | 0.400 |
| Fragrance | 1.500 |

Example 10

Body Lotion

A body lotion composition was prepared by combining the following ingredients. The amount of each ingredient is provided as percent by weight.

| Ingredient | W/W % Used |
|---|---|
| Water | QS to 100 |
| Hydroxypropyl Starch Phosphate Ester | 0.200 |
| Citric Acid | 0.100 |
| Aloe Barbadensis (Powder) | 0.001 |
| Grape Seed Extract (Powder) | 0.001 |
| Grape Skin Extract (Powder) | 0.001 |
| Green Tea Extract (Powder) | 0.001 |
| Glycerin | 3.000 |

-continued

| Ingredient | W/W % Used |
| --- | --- |
| Lactic Acid, Arginine | 1.000 |
| Glycerol Monostearate SE | 3.000 |
| Cetyl Alcohol | 4.000 |
| Stearic Acid | 4.000 |
| Cetearyl Glucoside | 2.000 |
| Melaleuca Oil | 0.001 |
| Octyl Palmitate | 3.000 |
| Polysorbate 20 | 2.500 |
| Evening Primrose Oil | 0.125 |
| Apricot Kernel Oil | 0.125 |
| Sunflower Seed Oil | 0.125 |
| Canola Oil | 0.125 |
| Decyl Oleate | 3.000 |
| Squalane | 4.500 |
| Saccharide Isomerate | 1.400 |
| Oat Extract | 0.100 |
| Ascorbyl Glucoside | 0.001 |
| Vitamin A & D3 Blend | 0.050 |
| d-Tocopherol Acetate | 0.050 |
| Grapefruit Seed Extract | 0.050 |
| Potassium Sorbate | 0.200 |
| Williams Pear Fruit Flakes | 0.400 |
| Raspberry Fruit Flakes | 0.400 |
| Fragrance | 1.500 |
| Carmine | 0.006 |

Example 11

Body Lotion

A body lotion composition was prepared by combining the following ingredients. The amount of each ingredient is provided as percent by weight.

| Ingredient | W/W % Used |
| --- | --- |
| Water | Q.S. to 100 |
| Citric Acid | 0.100 |
| Aloe Barbadensis (Powder) | 0.500 |
| Grape Seed Extract (Powder) | 0.100 |
| Green Tea Extract (Powder) | 0.500 |
| Glycerin | 3.000 |
| Lactic Acid, Arginine, and Water | 1.000 |
| Sodium Hydroxide | 0.750 |
| Glycerol Monostearate SE | 3.000 |
| Cetyl Alcohol | 4.000 |
| Stearic Acid | 4.000 |
| Cetearyl Glucoside | 2.000 |
| Melaleuca Oil | 0.250 |
| Octyl Palmitate | 3.000 |
| Polysorbate 20 | 2.500 |
| Dimethicone Copolyol | 1.500 |
| Evening Primrose Oil | 0.125 |
| Apricot Kernel Oil | 0.125 |
| Sunflower Seed Oil | 0.125 |
| Canola Oil | 0.125 |
| Decyl Oleate | 3.000 |
| Squalane | 4.500 |
| Saccharide Isomerate | 1.400 |
| Oat Extract | 0.100 |
| Ascorbyl Glucoside | 0.500 |
| Preservative | 0.900 |
| Vitamin A & D3 Blend | 0.050 |
| d-Tocopherol Acetate | 0.050 |
| Potassium Sorbate | 0.200 |
| Peach Fruit Flakes | 0.800 |
| Orange Fruit Flakes | 0.600 |
| Pure Vanilla Extract | 0.200 |
| Fragrance | 2.000 |

Example 12

Hand Cream

A hand cream composition was prepared by combining the following ingredients. The amount of each ingredient is provided as percent by weight.

| Ingredient | W/W % Used |
| --- | --- |
| Water | Q.S. to 100 |
| Aloe Barbadensis (Powder) | 0.100 |
| Grape Seed Extract (Powder) | 0.125 |
| Green Tea Extract (Powder) | 0.100 |
| Glycerin | 5.000 |
| Lactic Acid, Arginine | 1.000 |
| Glycerol Stearate SE | 3.500 |
| Isopropyl Myristate | 5.000 |
| Stearic Acid | 3.500 |
| Dimethicone Copolyol | 1.000 |
| Melaleuca Oil | 0.125 |
| Evening Primrose Oil | 0.050 |
| Apricot Kernel Oil | 0.050 |
| Sunflower Seed Oil | 0.050 |
| Canola Oil | 0.100 |
| Squalane | 4.000 |
| Oat Extract | 0.100 |
| Ascorbyl Glucoside | 0.090 |
| Vitamin A & D3 Blend | 0.400 |
| d-Tocopherol Acetate | 0.600 |
| Preservative | 0.100 |
| Potassium Sorbate | 0.200 |
| Golden Apple Fruit Flakes | 1.200 |
| Cranberry Fruit Flakes | 0.500 |
| Fragrance | 1.500 |
| Alfalfa Extract | 0.250 |

Example 13

Hand Cream

A hand cream composition was prepared by combining the following ingredients. The amount of each ingredient is provided as percent by weight.

| Ingredient | W/W % Used |
| --- | --- |
| Water | Q.S. to 100 |
| Carbomer | 0.200 |
| Aloe Barbadensis (Powder) | 0.500 |
| Grape Seed Extract (Powder) | 0.100 |
| Green Tea Extract (Powder) | 0.500 |
| Glycerin | 5.000 |
| Sodium lactate | 1.000 |
| Glycerol Stearate SE | 3.500 |
| Isopropyl Myristate | 5.000 |
| Stearic Acid | 3.500 |
| Dimethicone Copolyol | 1.000 |
| Melaleuca Oil | 0.001 |
| Evening Primrose Oil | 0.050 |
| Apricot Kernel Oil | 0.050 |
| Sunflower Seed Oil | 0.050 |
| Canola Oil | 0.100 |
| Squalane | 4.000 |
| Oat Extract | 0.100 |
| Ascorbyl Glucoside | 1.050 |
| Vitamin A & D3 Blend | 0.500 |
| d-Tocopherol Acetate | 0.050 |
| Preservative | 0.250 |
| Potassium Sorbate | 0.200 |
| Raspberry Fruit Flakes | 0.400 |
| Pear Fruit Flakes | 0.100 |
| Fragrance | 1.500 |

Example 14

Hand Cream

A hand cream composition was prepared by combining the following ingredients. The amount of each ingredient is provided as percent by weight.

| Ingredient | W/W % Used |
| --- | --- |
| Water | Q.S. to 100 |
| Hydroxypropyl Phosphate Starch Ester | 0.200 |
| Aloe Barbadensis (Powder) | 0.100 |
| Grape Seed Extract (Powder) | 0.001 |
| Green Tea Extract (Powder) | 0.001 |
| Glycerin | 5.000 |
| Lactic Acid, Arginine | 1.000 |
| Glycerol Stearate SE | 3.500 |
| Isopropyl Myristate | 5.000 |
| Stearic Acid | 3.500 |
| Dimethicone Copolyol | 1.000 |
| Melaleuca Oil | 0.001 |
| Evening Primrose Oil | 0.050 |
| Apricot Kernel Oil | 0.050 |
| Sunflower Seed Oil | 0.050 |
| Canola Oil | 0.100 |
| Squalane | 4.000 |
| Oat Extract | 0.100 |
| Ascorbyl Glucoside | 0.001 |
| Vitamin A & D3 Blend | 0.050 |
| d-Tocopherol Acetate | 0.050 |
| Grapefruit Seed Extract | 0.050 |
| Potassium Sorbate | 0.200 |
| Peach Fruit Flakes | 0.400 |
| Pure Vanilla Extract | 0.050 |
| BHT | 0.050 |
| Fragrance | 2.000 |

Example 15

Hand Cream

A hand cream composition was prepared by combining the following ingredients. The amount of each ingredient is provided as percent by weight.

| Ingredient | W/W % Used |
| --- | --- |
| Water | Q.S. to 100 |
| Aloe Barbadensis (Powder) | 0.500 |
| Grape Seed Extract (Powder) | 0.050 |
| Green Tea Extract (Powder) | 0.300 |
| Glycerin | 5.000 |
| Lactic Acid, Arginine | 1.000 |
| Glycerol Stearate SE | 3.500 |
| Isopropyl Myristate | 5.000 |
| Stearic Acid | 3.500 |
| Dimethicone Copolyol | 1.000 |
| Melaleuca Oil | 0.001 |
| Evening Primrose Oil | 0.050 |
| Apricot Kernel Oil | 0.050 |
| Sunflower Seed Oil | 0.050 |
| Canola Oil | 0.100 |
| Squalane | 4.000 |
| Oat Extract | 0.100 |
| Ascorbyl Glucoside | 2.000 |
| Vitamin A & D3 Blend | 0.050 |
| d-Tocopherol Acetate | 0.050 |
| Preservative | 0.150 |
| Potassium Sorbate | 0.200 |
| Orange Fruit Flakes | 0.800 |
| Cranberry Fruit Flakes | 0.600 |
| BHT | 0.050 |
| Fragrance | 1.500 |
| Paprika | 0.015 |

Example 16

Hand Soap

A hand soap composition was prepared by combining the following ingredients. The amount of each ingredient is provided as percent by weight.

| Ingredient | W/W % Used |
| --- | --- |
| Water | Q.S. to 100 |
| Hydroxypropyl Starch Phosphate Ester | 0.200 |
| Citric Acid | 0.300 |
| Green Tea Extract (Powder) | 0.100 |
| Aloe Barbadensis (Powder) | 0.400 |
| Grape Seed Extract (Powder) | 0.100 |
| Grape Skin Extract (Powder) | 0.100 |
| Polyquaternium 10 | 0.300 |
| Glycol Distearate | 0.900 |
| PEG-120 Glutamate | 5.000 |
| Glycerin | 5.000 |
| Sunflower Seed Oil | 0.060 |
| Canola Oil | 0.120 |
| Evening Primrose Oil | 0.060 |
| Apricot Oil | 0.060 |
| Disodium Oleamido MIPA Sulfosuccinate | 2.500 |
| Cocamidopropyl Betaine | 10.500 |
| Sodium Cocosulfate | 13.000 |
| Cetyl Alcohol | 0.500 |
| Lauric Acid | 1.000 |
| PEG-7 Glyceryl Cocoate | 2.000 |
| Polyglyceryl-3 Caprylate | 0.500 |
| Preservative | 0.500 |
| Vitamin A & D3 | 0.300 |
| Ascorbyl Palmitate | 0.001 |
| Dimethicone Copolyol | 0.500 |
| Melaleuca Oil | 0.020 |
| Potassium Sorbate | 0.200 |
| Apple Fibers | 0.400 |
| Apple Fruit Flakes | 1.000 |
| Cranberry Flakes | 0.300 |
| Fragrance | 4.000 |
| Alfalfa Extract | 0.030 |

Example 17

Hand Soap

A hand soap composition was prepared by combining the following ingredients. The amount of each ingredient is provided as percent by weight.

| Ingredient | W/W % Used |
| --- | --- |
| Water | Q.S. to 100 |
| Xanthan Gum | 0.200 |
| Citric Acid | 0.300 |
| Green Tea Extract (Powder) | 0.500 |
| Aloe Barbadensis (Powder) | 2.000 |
| Grape Skin Extract (Powder) | 0.125 |

-continued

| Ingredient | W/W % Used |
|---|---|
| Grape Seed Extract (Powder) | 0.500 |
| Polyquaternium 10 | 0.300 |
| Glycol Distearate | 0.900 |
| Glycerin | 1.000 |
| Sunflower Seed Oil | 0.060 |
| Canola Oil | 0.120 |
| Evening Primrose Oil | 0.125 |
| Apricot Oil | 0.125 |
| Disodium Oleamido MIPA Sulfosuccinate | 2.500 |
| Cocamidopropyl Betaine | 10.500 |
| Sodium Cocosulfate | 13.000 |
| Cetyl Alcohol | 0.500 |
| Lauric Acid | 1.000 |
| PEG-7 Glyceryl Cocoate | 2.000 |
| Polyglyceryl-3 Caprylate | 0.500 |
| d-Tocopheryl Acetate | 1.000 |
| Vitamin A & D3 | 0.450 |
| Ascorbyl Palmitate | 0.150 |
| Dimethicone Copolyol | 0.500 |
| Melaleuca Oil | 0.001 |
| Potassium Sorbate | 0.200 |
| Preservative | 0.300 |
| Pear Fruit Chunks | 0.900 |
| Raspberry Fruit Flakes | 0.900 |
| Fragrance | 4.000 |

Example 18

Hand Soap

A hand soap composition was prepared by combining the following ingredients. The amount of each ingredient is provided as percent by weight.

| Ingredient | W/W % Used |
|---|---|
| Water | Q.S. to 100 |
| Xanthan Gum | 0.200 |
| Citric Acid | 0.300 |
| Green Tea Extract (Powder) | 0.001 |
| Aloe Barbadensis (Powder) | 0.001 |
| Grape Seed Extract (Powder) | 0.001 |
| Polyquaternium 10 | 0.300 |
| Glycol Distearate | 0.900 |
| PEG-120 Glutamate | 0.001 |
| Glycerin | 1.000 |
| Sunflower Seed Oil | 0.060 |
| Canola Oil | 0.120 |
| Evening Primrose Oil | 0.060 |
| Apricot Oil | 0.060 |
| Disodium Oleamido MIPA Sulfosuccinate | 2.500 |
| Cocamidopropyl Betaine | 10.500 |
| Sodium Cocosulfate | 13.000 |
| Cetyl Alcohol | 1.000 |
| Lauric Acid | 1.000 |
| PEG-7 Glyceryl Cocoate | 2.000 |
| Polyglyceryl-3 Caprylate | 0.500 |
| d-Tocopheryl Acetate | 0.050 |
| Vitamin A & D3 | 0.001 |
| Ascorbyl Palmitate | 0.001 |
| Dimethicone Copolyol | 0.500 |
| Melaleuca Oil | 0.001 |
| Potassium Sorbate | 0.200 |
| Grapefruit Seed Extract | 0.050 |
| Exhausted Vanilla Bean Specks | 0.200 |
| Peach Fruit Flakes | 0.400 |
| Pure Vanilla Extract | 0.100 |
| Fragrance | 4.000 |

Example 19

Hand Soap

A hand soap composition was prepared by combining the following ingredients. The amount of each ingredient is provided as percent by weight.

| Ingredient | W/W % Used |
|---|---|
| Water | Q.S. to 100 |
| Citric Acid | 0.300 |
| Green Tea Extract (Powder) | 0.001 |
| Aloe Barbadensis (Powder) | 0.001 |
| Grape Seed Extract (Powder) | 0.001 |
| Polyquaternium 10 | 0.300 |
| Glycol Distearate | 0.900 |
| PEG-120 Glutamate | 5.000 |
| Glycerin | 1.000 |
| Sunflower Seed Oil | 0.060 |
| Canola Oil | 0.120 |
| Evening Primrose Oil | 0.060 |
| Apricot Oil | 0.060 |
| Disodium Oleamido MIPA Sulfosuccinate | 2.500 |
| Cocamidopropyl Betaine | 10.500 |
| Sodium Cocosulfate | 13.000 |
| Cetyl Alcohol | 0.500 |
| Lauric Acid | 1.000 |
| PEG-7 Glyceryl Cocoate | 2.000 |
| Polyglyceryl-3 Caprylate | 0.500 |
| d-Tocopheryl Acetate | 0.050 |
| Vitamin A & D3 | 0.250 |
| Ascorbyl Palmitate | 1.000 |
| Dimethicone Copolyol | 0.500 |
| Melaleuca Oil | 0.250 |
| Potassium Sorbate | 0.200 |
| Preservative | 0.450 |
| Apple Fibers | 0.500 |
| Orange Fruit Flakes | 0.400 |
| Pure Vanilla Extract | 0.100 |
| Fragrance | 4.000 |

Example 20

Hand Soap

A hand soap composition was prepared by combining the following ingredients. The amount of each ingredient is provided as percent by weight.

| Ingredient | W/W % Used |
|---|---|
| Water | Q.S. to 100 |
| Citric Acid | 0.300 |
| Green Tea Extract (Powder) | 0.450 |
| Aloe Barbadensis (Powder) | 0.350 |
| Grape Skin Extract (Powder) | 0.100 |
| Grape Seed Extract (Powder) | 0.050 |
| Polyquaternium 10 | 0.300 |
| Glycol Distearate | 0.900 |
| Glycerin | 1.000 |
| Sunflower Seed Oil | 0.060 |
| Canola Oil | 0.120 |
| Evening Primrose Oil | 0.060 |
| Apricot Oil | 0.060 |
| Disodium Oleamido MIPA Sulfosuccinate | 2.500 |
| Cocamidopropyl Betaine | 10.500 |
| Sodium Cocosulfate | 13.000 |
| Cetyl Alcohol | 0.500 |
| Lauric Acid | 1.000 |
| PEG-7 Glyceryl Cocoate | 2.000 |
| Polyglyceryl-3 Caprylate | 0.500 |

-continued

| Ingredient | W/W % Used |
|---|---|
| d-Tocopheryl Acetate | 0.350 |
| Vitamin A & D3 | 0.025 |
| Ascorbyl Palmitate | 0.015 |
| Dimethicone Copolyol | 0.500 |
| Melaleuca Oil | 0.001 |
| Potassium Sorbate | 0.200 |
| Preservative | 0.550 |
| Pear Fruit Chunks | 0.400 |
| Raspberry Fruit Flakes | 0.400 |
| Carmine | 0.090 |
| BHT | 0.050 |
| Fragrance | 4.000 |

Example 21

Lotion Assessment With or Without Fruit

Twenty participants were given three blind test samples to assess consumer-perceivable moisturization attributes. Three lotion compositions were prepared as described below. These compositions were prepared using the same ingredients, except that one was prepared without fruit and the other two contained two different levels of fruit (shown in bold text in the table below). All were identically packaged, and had the same color and scent characteristics. The twenty panelists blindly tested the three samples, and were asked to rate several different moisturizing attributes on a scale of 1 to 9:
1. How did your skin feel after the product was rubbed in to your skin?
   (1=dry/not silky; 9=very silky)
2. How was the texture of your skin after using the products?
   (1=rough; 9=smooth)
3. How moisturized did your skin feel after using the products?
   (1=not at all moisturized; 9=extremely moisturized)

Composition 1—Apple scented body lotion (no fruit flakes)
Composition 2—Apple scented body lotion (lower level of fruit flakes)
Composition 3—Apple scented body lotion (higher level of fruit flakes)

| Ingredients | W/W % Used (Composition 1) | W/W % Used (Composition 2) | W/W % Used (Composition 3) |
|---|---|---|---|
| Water | Q.S. to 100 | Q.S. to 100 | Q.S. to 100 |
| Hydroxypropyl Starch Phosphate Ester | 0.200 | 0.200 | 0.200 |
| Citric Acid | 0.100 | 0.100 | 0.100 |
| Aloe Barbadensis (Powder) | 0.001 | 0.001 | 0.001 |
| Grape Seed Extract (Powder) | 0.001 | 0.001 | 0.001 |
| Green Tea Extract (Powder) | 0.001 | 0.001 | 0.001 |
| Glycerin | 3.000 | 3.000 | 3.000 |
| Lactic Acid and Arginine | 1.000 | 1.000 | 1.000 |
| Glycerol Stearate SE | 3.000 | 3.000 | 3.000 |
| Cetyl Alcohol | 4.000 | 4.000 | 4.000 |
| Stearic Acid | 4.000 | 4.000 | 4.000 |
| Cetearyl Glucoside | 2.000 | 2.000 | 2.000 |
| Octyl Palmitate | 3.000 | 3.000 | 3.000 |
| Polysorbate 20 | 2.500 | 2.500 | 2.500 |
| Evening Primrose Oil | 0.125 | 0.125 | 0.125 |
| Apricot Kernel Oil | 0.125 | 0.125 | 0.125 |
| Sunflower Seed Oil | 0.125 | 0.125 | 0.125 |
| Canola Oil | 0.125 | 0.125 | 0.125 |
| Decyl Oleate | 3.000 | 3.000 | 3.000 |
| Squalane | 4.500 | 4.500 | 4.500 |
| Saccharide Isomerate | 1.400 | 1.400 | 1.400 |
| Oat Extract | 0.100 | 0.100 | 0.100 |
| Ascorbyl Glucoside | 0.001 | 0.001 | 0.001 |
| Vitamin A & D3 | 0.050 | 0.050 | 0.050 |
| d-Tocopherol Acetate | 0.050 | 0.050 | 0.050 |
| Grapefruit Seed Extract | 0.050 | 0.050 | 0.050 |
| Potassium Sorbate | 0.200 | 0.200 | 0.200 |
| Golden Apple Fruit Flakes | 0.000 | 0.400 | 1.000 |
| Cranberry Fruit Flakes | 0.000 | 0.100 | 0.200 |
| BHT | 0.050 | 0.050 | 0.050 |
| Fragrance | 1.500 | 1.500 | 1.500 |
| Sodium Copper Chlorophyllin | 0.006 | 0.006 | 0.006 |
| Alfalfa Extract | 0.050 | 0.050 | 0.050 |

Participants were asked to rub the products into their arms in three random places. The data were collected for statistical analysis by student's t-test. A P value less than 0.05 was considered statistically significant. The results were as follows:

| Samples | 1. Silky feel | 2. Softness of Skin | 3. Moisturized |
|---|---|---|---|
| No Fruit | 5.5 | 6.7 | 6.3 |
| Total fruit at 0.5% | 6.2 | 6.8 | 6.7 |
| Total fruit at 1.2% | 6.6 | 7.0 | 7.1 |
| IDEAL | 9.0 | 9.0 | 9.0 |
| T-test comparison | | | |
| No fruit vs. 0.5% | 0.12 | 0.92 | 0.25 |
| No fruit vs. 1.2% | 0.3 | 0.62 | 0.04* |
| 0.5% vs. 1.2% | 0.429 | 0.68 | 0.84 |

*p < 0.05

This survey clearly revealed a general trend that the fruit-containing compositions provided a silkier feeling, improved softness, and increased moisturization. Surprisingly, statistical differences were realized when the fruit concentration was about 1.2%, suggesting that the moisturization benefit can be realized within a short period with the fruit composition. A greater statistical difference might be achieved with a larger panel. The lack of a statistical difference between the no fruit formula and the formulation containing fruit at 0.5% may be due to having a good moisturization benefit from the base formula. For this reason, the product containing 0.5% fruit was tested against a similar and popular commercially available product that does not contain any fruit particles.

Example 22

Lotion Assessment of Fruit vs. Competitor's Product with Similar Scent

Thirty-two women between the ages of 18 and 60+ were solicited at a mall in the metropolitan New York area to test blind samples. An independent company performed this test. Respondents tested both fragranced lotions on the skin. The products were rotated evenly to prevent order bias, and were placed in identical containers with blind coded labels provided by Melaleuca. Each woman was tested separately and was asked to rate each product independently on a scale of 1 to 9 as described above. After both products had been rated, each woman was asked to compare the two lotions and give her preference between the two. Product A was an apple-scented lotion containing 0.5% fruit, disclosed as composition 2 in Example 22 above, while Product B was Bath and Body Works' Country Apple Moisture-Rich Body Lotion. The test result of moisture attributes are given below:

Product A

| FEEL AS RUBBED INTO SKIN: | |
|---|---|
| Average: | 7.38 |
| Top 2 box (8 or 9): | 63%—very silky |
| Bottom 2 box (1 or 2): | 0%—dry/not silky |
| HOW MUCH ABSORBED INTO SKIN? | |
| Average: | 7.16 |
| Top 2 box (8 or 9): | 63%—completely |
| Bottom 2 box (1 or 2): | 6%—not at all |
| HOW MOISTURIZED DID SKIN FEEL? | |
| Average: | 7.66 |
| Top 2 box (8 or 9): | 60%—extremely |
| Bottom 2 box (1 or 2): | 0%—not at all |

Product B

| FEEL AS RUBBED INTO SKIN: | |
|---|---|
| Average: | 5.47 |
| Top 2 box (8 or 9): | 22%—very silky |
| Bottom 2 box (1 or 2): | 18%—dry/not silky |
| HOW MUCH ABSORBED INTO SKIN? | |
| Average: | 6.53 |
| Top 2 box (8 or 9): | 50%—completely |
| Bottom 2 box (1 or 2): | 16%—not at all |
| HOW MOISTURIZED DID SKIN FEEL? | |
| Average: | 5.53 |
| Top 2 box (8 or 9): | 35%—extremely |
| Bottom 2 box (1 or 2): | 12%—not at all |
| COMPARISON: | |
| Preferred A: | 66% (21 panelists) |
| Preferred B: | 34% (11 panelists) |

The fruit-containing product was clearly preferred over the popular Bath and Body Works lotion, which was perceived to have a similar fragrance (and fragrance level), and also was perceived to be natural. The inclusion of fruit particles in skin care compositions thus can provide consumer-appreciated, increased moisturization capabilities as compared to compositions without fruit particles.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A skin care composition comprising fruit particles, wherein the fruit is selected from the group consisting of peach, strawberry, pear, sweet cherry, apricot, blackberry, papaya, mango, raspberry, cranberry, blueberry, kiwi, banana, grapefruit and vanilla bean, wherein said fruit particles are, by weight, from about 0.01% to about 1.4% of said composition; and wherein said skin care composition further comprises:
   a suspending agent at from about 0.01 to about 2% by weight of said composition, wherein said suspending agent is selected from a hydroxypropylated starch and a polycarboxylate polymer;
   an emulsifier;
   an emollient;
   an essential oil;
   a botanical extract;
   a vitamin; and
   a preservative; and wherein said skin care composition is a body lotion, cream, or moisturizer, a bath or shower gel, a body cleanser, an exfoliating body scrub, a bubble bath, or an after bath or shower body splash.

2. The skin care composition of claim 1, wherein said fruit particles are in suspension.

3. The skin care composition of claim 1, wherein said fruit particles comprise dried fruit.

4. The skin care composition of claim 1, wherein said fruit particles are in the form of a powder, flakes, or specks.

5. The skin care composition of claim 1, wherein said fruit particles have a tap density between about 0.1 g/mL and about 0.6 g/mL.

6. The skin care composition of claim 1, wherein said fruit particles have a tap density between about 0.2 g/mL and about 0.45 g/mL.

7. The skin care composition of claim 1, wherein said fruit particles are, by weight, from about 0.01% to about 1.0% of said composition.

8. The skin care composition of claim 1, wherein said fruit particles are, by weight, from about 0.1% to about 1.2% of said composition.

* * * * *